US008293462B2

(12) United States Patent
Eto et al.

(10) Patent No.: US 8,293,462 B2
(45) Date of Patent: Oct. 23, 2012

(54) METHOD OF PRESERVING EARLY MAMMALIAN EMBRYOS BY VITRIFICATION

(75) Inventors: Tomoo Eto, Kanagawa (JP); Erika Sasaki, Kanagawa (JP)

(73) Assignee: Central Institute for Experimental Animals, Kanagawa (JP)

( * ) Notice: Subject to any disclaimer, the term of this patent is extended or adjusted under 35 U.S.C. 154(b) by 859 days.

(21) Appl. No.: 12/197,076

(22) Filed: Aug. 22, 2008

(65) Prior Publication Data

US 2009/0123905 A1     May 14, 2009

Related U.S. Application Data

(62) Division of application No. 11/323,737, filed on Dec. 29, 2005, now abandoned.

(30) Foreign Application Priority Data

Oct. 17, 2005 (JP) .................................. 2005-301833

(51) Int. Cl.
*A01N 1/00* (2006.01)
(52) U.S. Cl. ........................................................ 435/1.1
(58) Field of Classification Search .................. None
See application file for complete search history.

(56) References Cited

U.S. PATENT DOCUMENTS 5,707,339 A   1/1998   Kameyama

FOREIGN PATENT DOCUMENTS

WO    WO 91/03935    4/1991

OTHER PUBLICATIONS

Edashige et al., "Restoration of Resistance to Osmotic Swelling of Vitrified Mouse Embryos by Short-Term Culture", Cryobiology 38 : 273-280 (1999).*
Dulbecco et al., "Plaque Formation and Isolation of Pure Lines with Poliomyelitis Viruses", J. Exp. Med. 99(2) : 167-182 (1954).*
J. Yoshino et al., "Cryopreservation of Porcine Blastocysts of Vitrification", Cryobiology 30, 413-422 (1993).
Non-final office action U.S. Appl. No. 11/323,737 dated May 22, 2008.
Fujioka, Tsuyoshi et al., "A simple and efficient cryopreservation method for primate embryonic stem cells", Int. J. Dev. Biol., vol. 48, pp. 1149-1154, 2004.
Han, M.-S. et al., "Vitrification of rat embryos at various developmental stages", Theriogenology 59, pp. 1851-1863, 2003.
Kasai, Magosaburo, "Vitrificaiton: Refined Strategy for the Cryopreservation of Mammalian Embryos", J. Mamm. Ova Res. vol. 14, pp. 17-28, 1997.
Nakagata, Naomi, "Cryopreservation of Unfertilized Rat Oocytes by Ultrarapid Freezing", Exp. Anim., vol. 41, No. 4, pp. 443-447, 1992.
Nakao, Kazuki et al., "Simple and Efficient Vitrification Procedure for Cryopreservation of Mouse Embryos", Exp. Anim., vol. 46, No. 3, pp. 231-234, 1997.
Rall, W. F. et al., "Ice-free cryopreservation of mouse embryos at --196o Cby vitrification", Nature, vol. 313, pp. 573-575, Feb. 14, 1985.
Reubinoff, B. E. et al., "Effective cryopreservation of human embryonic stem cells by the open pulled straw vitrification method", Human Reproduction, vol. 16, No. 10, pp. 2187-2194, 2001.
Richards, Mark et al., "An Efficient and Safe Xeno-Free Cryopreservatiuon Method for the Storage of Human Embryonic Stem Cells", Stem Cells, vol. 22, pp. 779-789, 2004.
Sato, Masahiro et al., "Successful vitricatiuon of stroke-prone spontaneously hypertensive and normal Wistar rat 2-cell embroyos", Laboratory Animals, vol. 30, pp. 132-137, 1996.
Whittingham, D.G. et al., "Survival of Rat Embryos After Freezing and Thawing", J. Reprod. Fert., vol. 43, pp. 575-578, 1975.
Sasaki, Erika et al., "Establishment of Novel Embryonic Stem Cell Lines Derived from the Common Marmoset (*Callithrix jacchus*)", Stem Cells, vol. 23, pp. 1304-1313, 2005.
Biochemicals, Organic Compounds for Research and Diagnostic Regents (Catalogue). 1994, Sigma Chemical Company, Sigma-Aldrich PTY LTD, Australia. See Product Information: Ficoll (Product No. F2637) p. 1433, & Percoll (Product No. P4937).
Chi, HJ, et al., "Cryopreservation of Human Embryos Using Ethylene Glycol in Controlled Slow Freezing", Human Reproduction, 2002, vol. 17, No. 8, pp. 2146-2151.
Gutierrez, A et al., "In Vitro Survival of Murine Morulae after Quick Freezing in the Presense of Chemically Defined Marcromolecules and different Cryoprotectants", Theriogenology, 1993, vol. 39, pp. 1111-1120.
Kasai, M. et al., "A Simple Method for Mouse Embryo Cryopreservation in a Low Toxicity Vitrofication Solution, Without Appreciable Loss of Viability", Journal of Reproduction and Fertility, 1990, vol. 89, No. 1, pp. 91-97.
Kasai, M et al., "Cryopreservation of Animal and Human Embryos by Vitrification" Reproductive BioMedicine Online, Aug. 2004, vol. 9, No. 2, pp. 164-170.
Miyamoto, H et al., "The Protective Action of Glycols against Freezing Damage of Mouse and Rat Embryos", Journal of Reproductive and Fertility, 1978, vol. 54, No. 2, pp. 427-432.
Pedro, PB et al., "Permaebility of Mouse Oocytes and Embryos at Various Developmental Stages to Five Cryoprotectants", Journal of Reproduction and Development, Apr. 2005, vol. 51, No. 2, pp. 235-246.
Singleton P & Sainsbury D (eds): Dictionary of Microbiology and Molecular Biology, 2nd edition, 1987, John Wiley & Sons, UK.
Whittingham, DG: "Survivial of Mouse Embryos after Freezing and Thawing" Nature, Sep. 1971, vol. 233, pp. 125-126.

(Continued)

*Primary Examiner* — Sandra Saucier
(74) *Attorney, Agent, or Firm* — Stephen A. Bent; Foley & Lardner LLP (57) ABSTRACT

This invention provides a solution for preserving mammalian early embryos or ES cells by vitrification, which comprises, as a base material, a phosphate buffer that exclusively contains 10% to 15% (v/v) propylene glycol as polyhydric alcohol or a phosphate buffer that exclusively contains 10% to 15% (v/v) propylene glycol and 25% to 35% (v/v) ethylene glycol as polyhydric alcohols and further contains 15% to 25% (v/v) Percoll® and 0.2 M to 0.5 M sucrose. This invention also provides a method for preserving mammalian early embryos or ES cells by vitrification using such solution.

8 Claims, 7 Drawing Sheets

(7 of 7 Drawing Sheet(s) Filed in Color)

OTHER PUBLICATIONS

Wusteman et al., "Vitrification of ECV304 Cell Suspensions Using Solutions Containing Propane-1,2,-diol and Trehalose", Cryobiology, vol. 46, pp. 135-145 (2003).

Search Resort for SG2006-0215-8, (2006).

Boutron et al, "Comparision of the Cryoptotection of Red Blood Cells by 1,2-Propanediol and Glycerol", Cryobiology, 21: 348-358 (1984).

Titterington et al, "The Proctective Action of Polyvinylpyrroloidone-Percoll During The Cryopreservatio of Mouse 2-cell embryos and its effect on subsequent developmental potential post-thaw in vitro and in vivo", Human Reproduction 11(12): 2697-2703 (1996).

Kasai, M., Cryopreservation of Mammalian Embryos by Vitrification, *In Perspectives on Assisted Reproduction,* Ares Serono Symposia Publications, Rome, Italy, 1994, pp. 481-487.

Eto et al., *Examination of a Method of Preserving Rat 2cell-stage embryos by vitrification,* The $52^{nd}$ Annual meeting of the Japanese Association for Laboratory Animal Science (JALAS), May 18-20, 2005, p. 158, Tokyo, Japan, Abstract.

\* cited by examiner

Teratomas were developed in blood vessels, muscles, and fats

No.20

Teratomas were developed in stratified squamous epithelium, hair shaft, follicles, and cartilage

METHOD OF PRESERVING EARLY MAMMALIAN EMBRYOS BY VITRIFICATION

This application is a divisional of U.S. application Ser. No. 11/323,737 filed on Dec. 29, 2005 now abandoned, which claims foreign priority benefits under Section 119(a)-(d) of Title 35 United States Code, to Japanese patent application no. JP2005-301833 as filed on Oct. 17, 2005, all of which are hereby expressly incorporated by reference.

TECHNICAL FIELD

The present invention relates to a method of preserving mammalian early embryos or ES cells by vitrification.

BACKGROUND ART

In experimental animal sciences and related industries, techniques for cryopreserving embryos are critical and fundamental for the production of animals or the preservation of cell lines via reproduction technology or the like. In the case of mice, the preservation of 2-cell-stage embryos has been already implemented because of the ease of sampling (see Nakao K. et al., Exp. Anim. 46(3), 231-234, 1997).

When early embryos, such as rat 2-cell-stage embryos, are preserved, however, the rate of retrieval is poor. Such preservation does not yield a rate of fetal development similar to that obtained from untreated embryos (see D. G. Whittingham, J. Reprod. Fert, 1975, 43, 575-578; and M. S. Han et al., Theriogenology 59, 2003, 1851-1863). Thus, there are many issues to be resolved regarding techniques for cryopreserving experimental animal embryos.

In contrast, it has been expected that primate ES cells are put to clinical use, such as the study of development, the preparation of genetically engineered animals, or the regenerative medical techniques. In order to effectively utilize such ES cells for the aforementioned purposes, it is necessary to multiply these cells to a great extent, preserve the multiplied cells, and provide the amount required at the time of use. Further, cell culture usually involves the risk of a mutation of traits, which necessitates preservation of some established cells. Several techniques for preserving primate ES cells have been already reported. A method that yields a high rate of cell survival (see Reubinoff B. E. et al., 2001, Human Reprod. Vol. 16, No. 10, 2187-2194), however, can preserve only approximately 20 to 30 ES cell clumps. A method that can simultaneously preserve a large number of ES cells is available (see Fujioka, T. et al., 2004, Int. J. Dev. Biol., 48: 1149-1154), although the rate of cell survival after thaw is as low as 10% to 20%. Accordingly, development of a method that enables simultaneous preservation of a large number of ES cells, yields a high rate of cell survival after thaw, and allows maintenance of an undifferentiated state has been awaited.

It has been known that direct introduction of a solution with a high content of cryoprotective agent into liquid nitrogen or liquid nitrogen gas results in vitrification of a solution rather than crystallization thereof. The term "vitrification" substantially refers to a phenomenon where a solution becomes solidified instead of being crystallized. A variety of techniques have been developed to preserve animal cells via vitrification. However, there has been no preservation technique for rat early embryos or mammalian ES cells that can yield a high rate of cell retrieval.

DISCLOSURE OF THE INVENTION

The present invention provides a solution for preserving animal early embryos or ES cells by vitrification and a method for preserving such cells by vitrification.

The present inventors have conducted concentrated studies concerning preservation of rat 2-cell-stage embryos and primate ES cells. They developed a novel solution that is suitable for preserving mammalian early embryos or ES cells by vitrification. They also developed a method for preservation by vitrification using such solution, thereby completing the present invention.

Specifically, the present invention is as follows.

[1] A solution for preserving mammalian early embryos or ES cells by vitrification comprising, as a base material, a phosphate buffer that exclusively contains 10% to 15% (v/v) propylene glycol as polyhydric alcohol.

[2] A solution for preserving mammalian early embryos or ES cells by vitrification comprising, as a base material, a phosphate buffer that exclusively contains 10% to 15% (v/v) propylene glycol and 25% to 35% (v/v) ethylene glycol as polyhydric alcohols and further contains 15% to 25% (v/v) Percoll® and 0.2 M to 0.5 M sucrose.

[3] The solution for preserving mammalian early embryos or ES cells by vitrification according to [1] comprising 700 to 900 mg/100 ml NaCl, 15 to 25 mg/100 ml KCl, 8 to 15 mg/100 ml $CaCl_2$, 15 to 25 mg/100 ml $KH_2PO_4$, 7.5 to 12.5 mg/100 ml $MgCl_2.6H_2O$, 100 to 130 mg/100 ml $Na_2HPO_4$, 3 to 4 mg/100 ml Na pyruvate, 75 to 125 mg/100 ml glucose, 5 to 10 mg/100 ml antibiotics, 250 to 350 mg/100 ml BSA, and 10% to 15% (v/v) propylene glycol.

[4] The solution for preserving mammalian early embryos or ES cells by vitrification according to [2] comprising 700 to 900 mg/100 ml NaCl, 15 to 25 mg/100 ml KCl, 8 to 15 mg/100 ml $CaCl_2$, 15 to 25 mg/100 ml $KH_2PO_4$, 7.5 to 12.5 mg/100 ml $MgCl_2.6H_2O$, 100 to 130 mg/100 ml $Na_2HPO_4$, 3 to 4 mg/100 ml Na pyruvate, 75 to 125 mg/100 ml glucose, 5 to 10 mg/100 ml antibiotics, 250 to 350 mg/100 ml BSA, 10% to 15% (v/v) propylene glycol, 25% to 35% (v/v) ethylene glycol, 15% to 25% (v/v) Percoll®, and 0.2 M to 0.5 M sucrose.

[5] A solution for preserving mammalian early embryos or ES cells by vitrification comprising a solution consisting of 700 to 900 mg/100 ml NaCl, 15 to 25 mg/100 ml KCl, 8 to 15 mg/100 ml $CaCl_2$, 15 to 25 mg/100 ml $KH_2PO_4$, 7.5 to 12.5 mg/100 ml $MgCl_2.6H_2O$, 100 to 130 mg/100 ml $Na_2HPO_4$, 3 to 4 mg/100 ml Na pyruvate, 75 to 125 mg/100 ml glucose, 5 to 10 mg/100 ml antibiotics, and 250 to 350 mg/100 ml BSA, with the solution for preservation by vitrification according to [4] dissolved therein at a concentration of 75% to 100% (v/v).

[6] The solution for preservation by vitrification according to any of [1] to [5], wherein the mammalian early embryos are mammalian 2-cell-stage embryos.

[7] The solution for preservation by vitrification according to [6], wherein the mammalian 2-cell-stage embryos are rat 2-cell-stage embryos and the mammalian ES cells are primate ES cells.

[8] A reagent kit for preserving mammalian early embryos or ES cells by vitrification comprising the solution according to [1] or [3] and the solution according to [2], [4], or [5].

[9] The reagent kit for preserving mammalian early embryos or ES cells by vitrification according to [8], which further comprises a cell-thawing solution for the mammalian early embryos or ES cells preserved by vitrification containing, as a base material, a phosphate buffer containing 0.2 M to 0.5 M sucrose.

[10] The reagent kit for preserving mammalian early embryos or ES cells by vitrification according to [9], which comprises a cell-thawing solution for the mammalian early embryos or ES cells preserved by vitrification containing, as a base material, a phosphate buffer consisting of 700 to 900 mg/100 ml NaCl, 15 to 25 mg/100 ml KCl, 8 to 15 mg/100 ml CaCl$_2$, 15 to 25 mg/100 ml KH$_2$PO$_4$, 7.5 to 12.5 mg/100 ml MgCl$_2$.6H$_2$O, 100 to 130 mg/100 ml Na$_2$HPO$_4$, 3 to 4 mg/100 ml Na pyruvate, 75 to 125 mg/100 ml glucose, 5 to 10 mg/100 ml antibiotics, 250 to 350 mg/100 ml BSA, and 0.2 M to 0.5 M sucrose.

[11] The reagent kit for preservation by vitrification according to any of [8] to [10], wherein the mammalian early embryos are mammalian 2-cell-stage embryos.

[12] The reagent kit for preservation by vitrification according to [11], wherein the mammalian 2-cell-stage embryos are rat 2-cell-stage embryos and the mammalian ES cells are primate ES cells.

[13] A method of preserving mammalian early embryos or ES cells by vitrification comprising steps of pretreating mammalian early embryos or ES cells in the solution for preservation by vitrification according to [1] or [3] and cryopreserving the cells in the solution for preservation by vitrification according to [2], [4], or [5].

[14] The method of preserving mammalian early embryos or ES cells by vitrification according to [13], wherein mammalian early embryos or ES cells are immersed in the solution for preservation by vitrification according to [1] or [3] at room temperature for 5 to 10 minutes, the solution is then allowed to stand at 0° C. to 5° C. for 30 seconds to 2 minutes, and the resulting solution is cryopreserved in 40 to 60 times its volume of the solution for preservation by vitrification according to [2], [4], or [5].

[15] The method of preserving mammalian early embryos or ES cells by vitrification according to [13] or [14], wherein the mammalian early embryos are mammalian 2-cell-stage embryos.

[16] The method of preserving mammalian early embryos or ES cells by vitrification according to [15], wherein the mammalian 2-cell-stage embryos are rat 2-cell-stage embryos and the mammalian ES cells are primate ES cells.

The solution for preservation by vitrification according to the present invention is suitably used for preserving animal early embryos or ES cells, such as rat 2-cell-stage embryos or primate ES cells. When animal early embryos or ES cells are cryopreserved via the method of preservation by vitrification according to the present invention that employs the solution for preservation by vitrification according to the present invention, high rates of cell survival and of cell retrieval can be achieved after thaw.

BRIEF DESCRIPTION OF THE DRAWINGS

The application contains at least one drawing executed in color. Copies of this patent or patent application publication with color drawing(s) will be provided by the Office upon request and payment of the necessary fee.

PREFERRED EMBODIMENTS OF THE INVENTION

The solution for preserving mammalian early embryos or ES cells by vitrification according to the present invention comprises, as a base material, a phosphate buffer. Examples of such solution include P10 comprising a modified phosphate buffer (PB1) and propylene glycol and PEPeS comprising PB1, propylene glycol, ethylene glycol, Percoll®, and sucrose.

PB1 comprises: 700 to 900 mg/100 ml, and preferably 800 mg/ml, NaCl; 15 to 25 mg/100 ml, and preferably 20 mg/ml, KCl; 8 to 15 mg/100 ml, and preferably 12 mg/100 ml, CaCl$_2$; 15 to 25 mg/100 ml, and preferably 20 mg/100 ml, KH$_2$PO$_4$; 7.5 to 12.5 mg/100 ml, and preferably 10 mg/100 ml, MgCl$_2$.6H$_2$O; 100 to 130 mg/100 ml, and preferably 115 mg/100 ml, Na$_2$HPO$_4$; 3 to 4 mg/100 ml, and preferably 3.6 mg/100 ml, Na pyruvate; 75 to 125 mg/100 ml, and preferably 100 mg/100 ml, glucose; 5 to 10 mg/100 ml, and preferably 7.5 mg/100 ml, penicillin G; and 250 to 350 mg/100 ml, and preferably 300 mg/100 ml, BSA. A typical type of PB1 has the composition as shown in Table 1.

P10 is prepared by adding 5% to 15% (v/v), preferably 10% to 15% (v/v), and particularly preferably 10% (v/v) propylene glycol to PB1. PEPeS is prepared by adding 5% to 15% (v/v), preferably 10 to 15% (v/v), and particularly preferably 10% (v/v), propylene glycol; 25% to 35% (v/v), and preferably 30% (v/v), ethylene glycol; 15% to 25% (v/v), and preferably 20% (v/v), Percoll®(g; and 0.2M to 0.5M, and preferably 0.3M, sucrose to PB1. The solution for preservation by vitrification according to the present invention does not contain glycerol or polyethylene glycol. It exclusively contains propylene glycol or propylene glycol and ethylene glycol as polyhydric alcohols. The solution for preservation by vitrification according to the present invention does not contain dimethyl sulfoxide. PEPeS may be further mixed with PB1 and used at PEPeS concentration of 50% to 100% (v/v), and preferably 75% to 100% (v/v).

The aforementioned solution may comprise other antibiotics, such as streptomycin or gentamycin, instead of penicillin G, and it may be composed of a plurality of constituents. Also, the solution may comprise fetal serum from horse, sheep, goat, or the like, instead of BSA (i.e., bovine serum albumin).

In the present invention, the target cells to be preserved by vitrification are mammalian early embryos, although the animal species or embryonic stages are not limited. Animal species are preferably rodents or primates, and rodents, particularly rats, are more preferable. 2-cell-stage embryos are preferable. The target of preservation by vitrification according to the present invention includes mammalian ES cells. ES cells are mammalian ES cells, and preferably primate ES cells. Mammalian embryos can be obtained in accordance with a conventional technique, and mammalian ES cells can be established in accordance with a conventional technique.

In the present invention, preservation by vitrification involves the use of the aforementioned P 10 and PEPeS solutions.

When it is intended to preserve mammalian embryos by vitrification, mammalian embryos are immersed in the P10 solution for preservation by vitrification for 10 to 20 minutes, preferably 3 to 15 minutes, and more preferably 5 to 10 minutes. Immersion may be carried out at room temperature (22° C. to 25° C.). Subsequently, the embryos, which had been subjected to immersion as a step of pretreatment, are introduced into a cryopreservation tube with the P10 solution, and the resultant is cooled at 0° C. to 5° C., and preferably 0° C., for several tens of seconds to minutes, preferably 30 seconds to 2 minutes, and more preferably 1 minute. Thereafter, the cells are kept in P10, introduced into the PEPeS solution for preservation by vitrification in that state, and then frozen at a low temperature of −196° C. or lower. Freezing may be carried out with the use of, for example, liquid nitrogen. The volume ratio of embryo-containing P10 to embryo-containing PEPeS is 1:99 to 20:80, preferably 2.5:97.5 to 10:90, and more preferably 5:95. Alternatively, P10 that contains embryos to be frozen is introduced into 4 to 100, preferably 10 to 75, more preferably 40 to 60, and particularly preferably 45 times its volume of PEPeS. The P10 solution according to the present invention is used for pretreatment at the time of preservation of embryos or ES cells by vitrification. Thus, this solution can also be referred to as a "pretreatment solution for preservation by vitrification."

The embryos or ES cells that were cryopreserved by the method of preservation by vitrification according to the present invention may be treated in the following manner. For example, a freezing tube containing frozen embryos or ES cells is removed from liquid nitrogen and is then allowed to stand at room temperature for 10 to 60 seconds, and preferably for about 30 seconds. Thereafter, 5 to 10 times its volume of a cell-thawing solution maintained at room temperature is introduced into the tube, cells are thawed, and the embryos or ES cells may be then washed with a cell-thawing solution. A cell-thawing solution is not limited. An example of such solution can be obtained by adding 0.2 M to 0.5 M, and preferably 0.3 M, sucrose to the aforementioned PB1.

The embryos that were cryopreserved by the method of the present invention exhibit a high rate of survival after thaw and a high rate of fetal development after embryonic transplantation. Also, the ES cells that were cryopreserved by the method of the present invention exhibit a high rate of survival after thaw and maintain a multipotent state.

The present invention further includes a reagent kit for preserving mammalian early embryos or ES cells by vitrification that comprises the aforementioned P10 solution for preservation by vitrification separately from the PEPeS solution for preservation by vitrification. This kit first uses the P10 solution for preservation by vitrification to subject mammalian early embryos or ES cells to pretreatment and introduces the mammalian early embryos or ES cells into PEPeS for cryopreservation, as mentioned above.

This method of the present invention may be referred to as the "CIEA method."

EXAMPLES

The present invention is hereafter described in greater detail with reference to the following examples, although the technical scope of the present invention is not limited thereto.

Example 1

Preservation of Rat 2-Cell-Stage Embryos by Vitrification

Rat 2-cell-stage embryos were used. Brl Han:Wist@Jcl (GALAS) rats were employed. 8-12-week-old female rats and 12-24-week-old male rats were employed. As test embryos, 2-cell-stage embryos obtained from female rats that had been subjected to superovulation followed by natural mating were employed. Specifically, 150 IU/kg of PMGS was injected intraperitoneally into female rats and 75 IU/kg of hCG was injected intraperitoneally 48 hours thereafter. Rats were subjected to mating immediately after the injection of hCG, smears were sampled the following morning, and the estrous cycle and sperm impregnation were confirmed. The 2-cell-stage embryos were sampled from female rats having positive smears via perfusion of the oviducts 45 hours after the injection of hCG. The sampled embryos were cultured at 37° C. in 5% $CO_2$ and 95% air for approximately 1 hour and then subjected to the test.

The P10 solution, which comprises the PB1 solution of modified phosphate buffer (Table 1) and 10% propylene glycol, and the PEPeS solution, which comprises the PB1 solution, 10% propylene glycol, 30% ethylene glycol, 20% Percoll®, and 0.3 M sucrose, were employed for vitrification. A solution (SPB1), which comprises PB1 and 0.3 M sucrose, was used for heating.

TABLE 1

| Phosphate buffer 1 (PB1) | |
|---|---|
| Reagent | mg/100 ml |
| NaCl | 800.0 |
| KCl | 20.0 |
| $CaCl_2$ | 12.0 |
| $KH_2PO_4$ | 20.0 |
| $MgCl_2 \cdot 6H_2O$ | 10.0 |
| $Na_2HPO_4$ | 115.0 |
| Na pyruvate | 3.6 |
| Glucose | 100.0 |
| Penicillin G | 7.5 |
| BSA | 300.0 |

Preservation by vitrification was carried out in the following manner. The 2-cell-stage embryos were immersed in 100 µl of P10 at room temperature (22° C. to 25° C.) for 5 minutes as a step of pretreatment. Subsequently, early embryos were introduced into a preservation tube (Nunc 375353) with 5 µl of P10, followed by cooling at 0° C. for 1 minute. Thereafter, 95 µl of PEPeS, which had been cooled to 0° C., was introduced into the tube. After the tube was allowed to stand at 0° C. for 1 minute, the tube was introduced into the liquid phase of liquid nitrogen ($LN_2$) for preservation by vitrification.

The preserved early embryos were thawed in the following manner. The tube was transferred from $LN_2$ to room temperature conditions, 900 µl of SPB1 was introduced approximately 30 seconds thereafter, and pipetting was then carried out 4 or 5 times immediately thereafter. Subsequently, the thawed solution was transferred to a petri dish, and the early embryos were recovered with the use of an egg-sampling pipette. The recovered cell clumps were transferred into PB1, allowed to stand for 2 minutes, washed two times with the PB1 solution, and then subjected to the subsequent test.

Examination of Pretreatment

The embryos were immersed in P10 for 5 or 10 minutes, transferred into SPB1, and washed three times with PB1 2 minutes thereafter. Thereafter, cell survival was inspected via morphological observation of embryos under a microscope. The surviving embryos were subjected to embryo transplantation, and fetal development was inspected.

The rates of embryo survival (Table 2) were 100% in both cases. The percentages of fetuses experiencing development (Table 3) were also high in the cases of immersion for 5 minutes or 10 minutes (i.e., 72.4% to 81.7%). This indicates that immersion of embryos in the pretreatment solution does not influence the embryo development thereafter, if immersion takes place for 5 to 10 minutes.

TABLE 2

Rate of embryo survival after pretreatment

| Pretreatment time (min) | Number of pretreated embryos | Number (%) of morphologically normal embryos |
|---|---|---|
| 5 | 76 | 76 (100.0) |
| 10 | 60 | 60 (100.0) |

TABLE 3

Development of pretreated embryos in uterine

| Pretreatment time (min) | Number of transplanted embryos | Number (%) of fetuses experiencing development |
|---|---|---|
| Control | 50 | 39 (78.0) |
| 5 | 76 | 55 (72.4) |
| 10 | 60 | 49 (81.7) |

Examination of Preservation by Vitrification

Pretreatment was carried out by immersing the embryos in P10 for 2, 5, or 10 minutes. A control embryo, which had not been treated with P10, was provided. Thereafter, the embryos were transferred to a tube with 5 µl of the solution, followed by cooling at 0° C. for 1 minute. Subsequently, 95 µl of PEPeS (0° C.) was introduced into the tube, and the tube was introduced into liquid nitrogen 1 minute later for vitrification. After the tube was transferred from liquid nitrogen to room temperature conditions, 900 µl of SPB1 (37° C.) was introduced thereinto 30 seconds thereafter, and pipetting was then carried out approximately 10 times for heating. The recovered embryos were introduced into the PB1 solution and washed three times with the same solution 2 minutes thereafter. Thereafter, cell survival was inspected via morphological observation of embryos under a microscope. The surviving embryos were subjected to embryo transplantation, and fetal development was inspected.

Except for the control embryo that had not been treated with P10 (63.3%), the rates of embryo survival that had been pretreated with P10 were high (i.e., 92.0% to 93.6%, Table 4). This revealed that immersion of embryos in P10 as a step of pretreatment would improve embryo survival after thaw. The percentages of fetuses developed from thawed embryos (Table 5), which had not been treated with P10, was 0%. When embryos were pretreated with P10, the rate of development was 45.5% to 65.2%, and the highest rate was obtained when the embryos were treated for 5 minutes.

TABLE 4

Survival rate of cryopreserved 2-cell-stage embryo after heating

| Pretreatment time (min) | Number of vitrified embryos | Number (%) of morphologically normal embryos |
|---|---|---|
| 0 | 120 | 76 (63.3) |
| 2 | 141 | 132 (93.6) |
| 5 | 125 | 115 (92.0) |
| 10 | 125 | 116 (92.8) |

TABLE 5

Development of cryopreserved 2-cell-stage embryos in uterine

| Immersion time (min) | Number of transplanted embryos | Number (%) of fetuses experiencing development |
|---|---|---|
| Control | 105 | 82 (78.1) |
| 0 | 76 | 0 (0.0) |
| 2 | 132 | 60 (45.5) |
| 5 | 115 | 75 (65.2) |
| 10 | 116 | 69 (59.5) |

As is apparent from the above results, a method of vitrifying embryos after immersing them in P10 for 5 minutes is effective for preserving rat 2-cell-stage embryos when a novel solution for preservation by vitrification is used.

Example 2

Preservation of Marmoset ES Cells by Vitrification

As marmoset ES cells, two cell lines, i.e., No. 40 and No. 20, which were established by the Central Institute for Experimental Animals (Japan), were employed (Sasaki E. et al., 2005, Establishment of Novel Embryonic Stem Cell Lines Derived from the Common Marmoset (*Callithrix jacchus*), Stem Cells. (in press)). The cell clumps separated via trypsin treatment were recovered with an egg-sampling pipette and used in the preservation experiment.

In the method of preservation by vitrification according to the present invention, the P10 pretreatment solution comprising PB1 and 10% propylene glycol and the PEPeS solution comprising PB1, 10% propylene glycol, 30% ethylene glycol, 20% Percoll®(t, and 0.3 M sucrose were used. In thaw, the SPB1 solution comprising PB1 and 0.3 M sucrose was used.

In preservation of the control embryos by vitrification (Fujioka T. et al., Int. J. Dev. Biol. 48: 1149-1154), a DAP213 solution comprising PB1, 2 mol of DMSO, 1 mol of acetamide, and 3 mol of propylene glycol was used. In slow freezing (Reubinoff B. E. et al., Human Reprod. Vol. 16, No. 10, 2187-2194), the SF solution comprising 10% DMSO in FCS was used.

ES cells were preserved and thawed in the following manner.

Cell clumps were immersed in 1 ml of P10 at room temperature (22° C. to 25° C.) for 5 minutes as a step of pretreatment. Subsequently, the cell clumps were introduced into a preservation tube (Nunc 375353) with 5 µl of P10, followed by cooling at 0° C. for 1 minute. Thereafter, 95 µl of PEPeS, which had been cooled to 0° C., was introduced into the tube. After the tube was allowed to stand at 0° C. for 1 minute, the tube was introduced into the liquid phase of liquid nitrogen ($LN_2$) for preservation by vitrification. The preserved cell clumps were thawed in the following manner. The tube was transferred from $LN_2$ to room temperature conditions, 900 µl of SPB1 was introduced approximately 30 seconds thereafter, and pipetting was then carried out 4 or 5 times immediately thereafter. Subsequently, the thawed solution was transferred to a petri dish, and the cell clumps were recovered with the use of an egg-sampling pipette. The recovered cell clumps were transferred into PB1 and allowed to stand for 2 minutes. Culture was initiated thereafter.

Preservation of the control embryos by vitrification (Fujioka T. et al., Int. J. Dev. Biol. 48: 1149-1154) was carried out by introducing the cell clumps into 200 µl of DAP213 followed by cooling in $LN_2$ 15 seconds later. Thaw was carried out by transferring the tube preserved in LN$_2$ to room temperature conditions and introducing 900 µl of PB1 at 37° C., followed by pipetting. Slow freezing was carried out by introducing the cell clumps into 100 µl of the SF solution at room temperature, cooling the cell clumps to −80° C. at a rate of 1° C./min, and introducing the resultant into O/N and then into LN$_2$. Culture of the preserved cell clumps was initiated after removing the tube from LN$_2$. The cell clumps were thawed in a water bath at 37° C. and then washed with PB1.

In all the experiments, 50 cell clumps were introduced into a tube and then preserved in the liquid phase of LN$_2$ for 7 days. Several tubes of the same type were used.

Determination of the Concentration of the Solution for Preservation by Vitrification In order to examine the P10 concentration, propylene glycol was added to PB11 at concentrations of 0%, 5%, 10%, and 15%. The cell clumps of No. 40 were preserved in the resulting solutions. In order to examine the PEPeS concentration, PEPeS was diluted with PB1 to 75%, 50%, and 0%, and the cell clumps were preserved in the resulting dilutions. After preservation, the cell clumps were heated, culture was then initiated, and the survival rates of cell clumps was observed under an inverted microscope 4 days thereafter.

Figure 1:
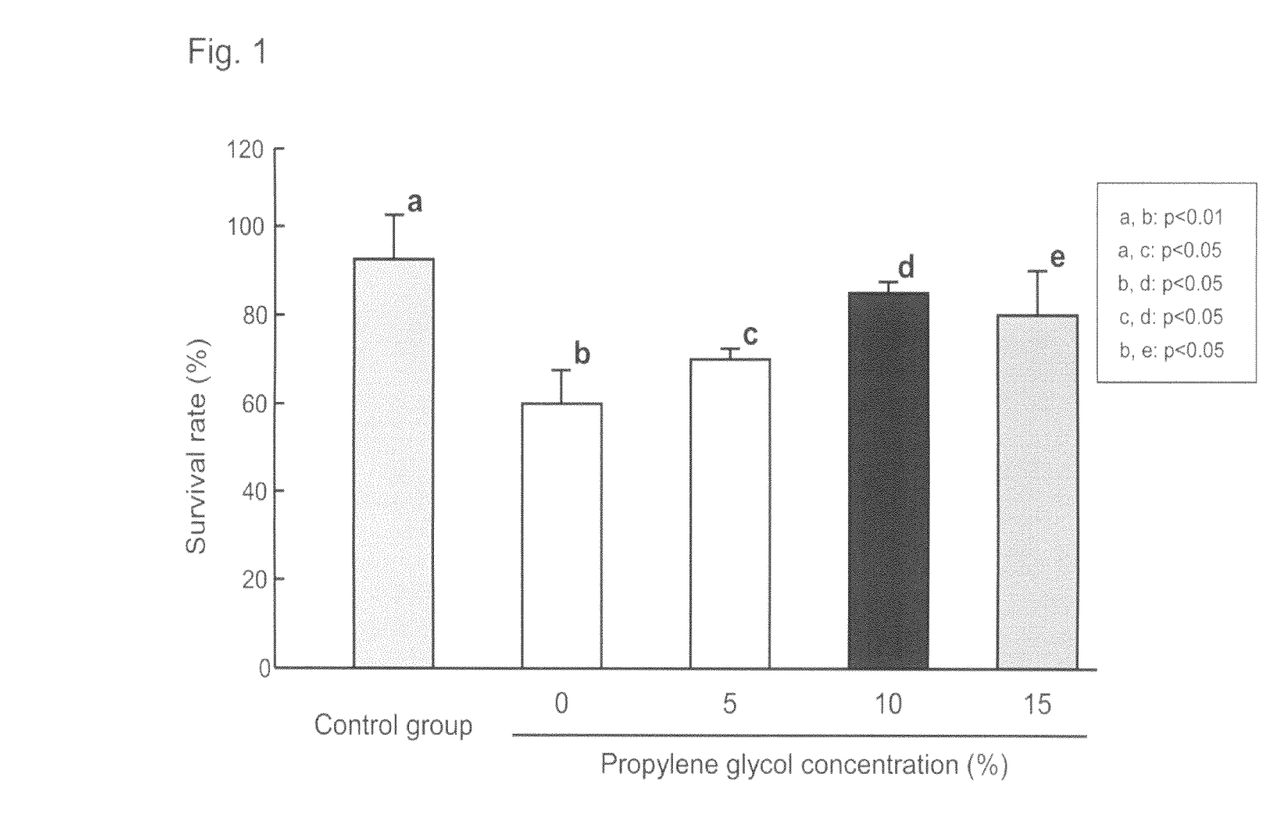
FIG. 1 shows the correlation between the survival rates of ES cells after thaw and propylene glycol concentration in P10.

Through the examination of P10 concentration (FIG. 1), the survival rate of the embryos preserved in 0% and 5% solutions was found to be significantly lower than that of the control embryos that had not been preserved. In contrast, the embryos preserved in the 10% (P10) and 15% solutions did not differ from the control embryos. This indicates that a solution containing 10% to 15% propylene glycol is optimal for preservation of cells by vitrification. A cryoprotective agent usually induces cytotoxicity as the concentration is raised. Thus, a solution with the lowest propylene glycol concentration of 10% was employed.

Figure 2:
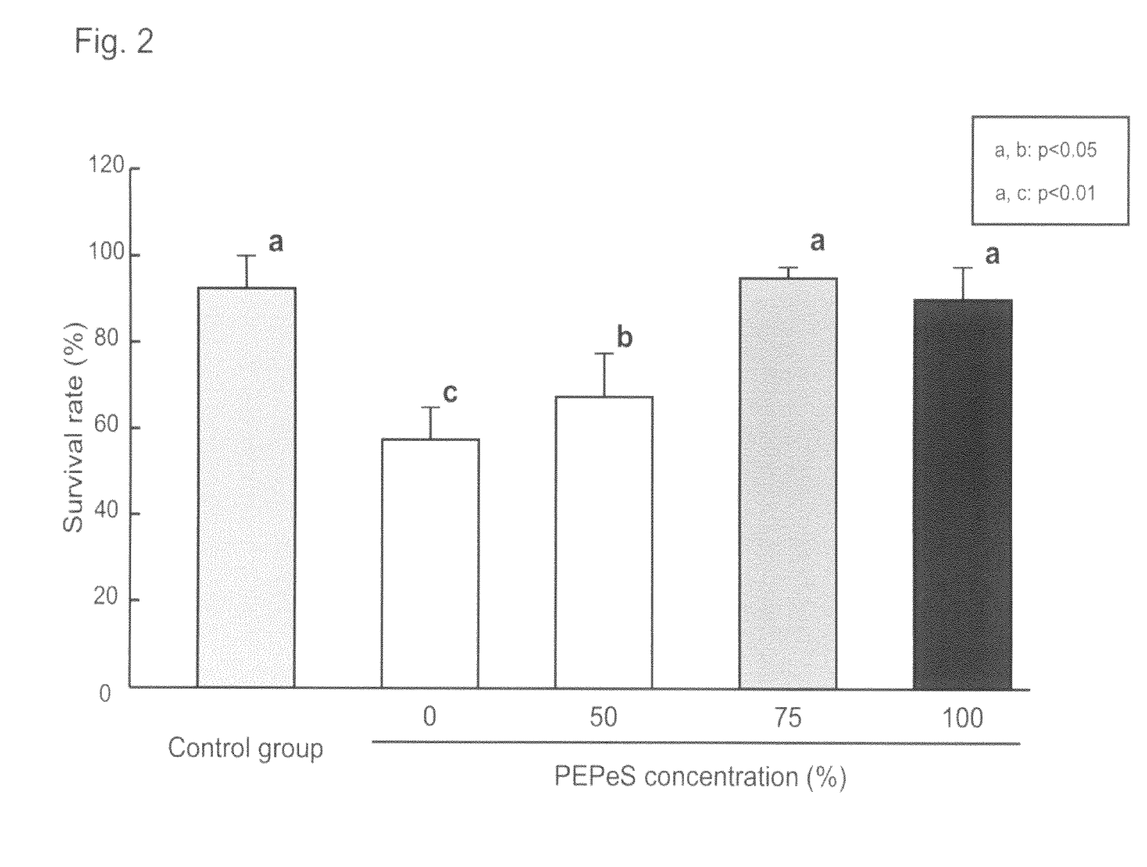
FIG. 2 shows the correlation between the survival rates of ES cells after thaw and PEPeS concentration.
Figure 3:
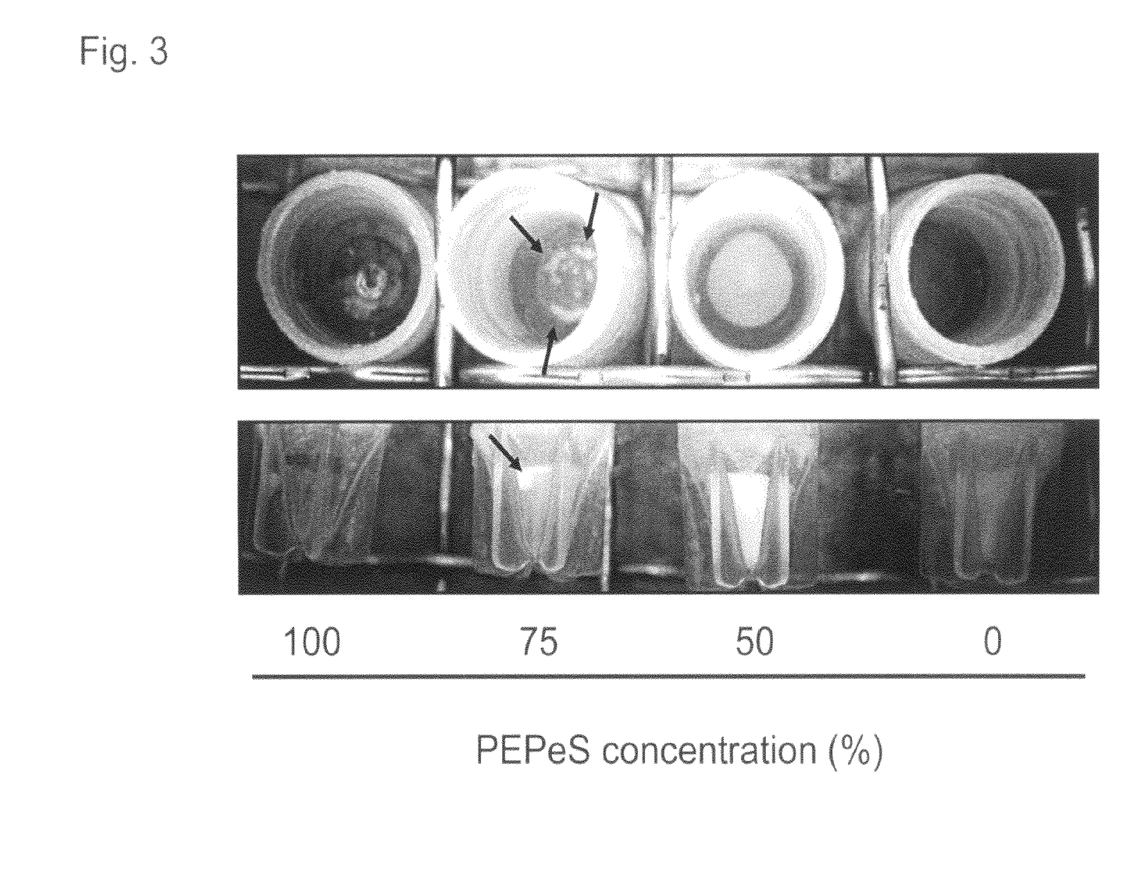
FIG. 3 shows conditions of a solid surface influenced by PEPeS concentration.

Through the examination of PEPeS concentration (FIG. 2), the survival rate of the embryos preserved in a solution with PEPeS concentration of 0% or 50% was found to be significantly lower than that of the control embryos. In contrast, the embryos preserved in a solution with PEPeS concentration of 100% or 75% did not significantly differ from the control embryos. This indicates that a solution with PEPeS concentration of 100% to 75% is effective for preservation. However, a lowered PEPeS concentration leads to the devitrification of the solution. White spots were observed on the vitrified surface, particularly in a solution with PEPeS concentration of 75% (FIG. 3). This indicates that part of the solution became crystallized, which indicates that the preservation conditions in the tube were not homogenous. Thus, a solution with PEPeS concentration of 100% was employed for preservation.

Comparison with Other Preservation Techniques

The cell line No. 40 was used to compare the method of the present invention with conventional techniques. The method of the present invention, a method of vitrification with the use of DAP213, or slow freezing was employed for preservation. Comparison was carried out by observing the number of surviving cell clumps under an inverted microscope 4 days after the initiation of culture.

Figure 4:
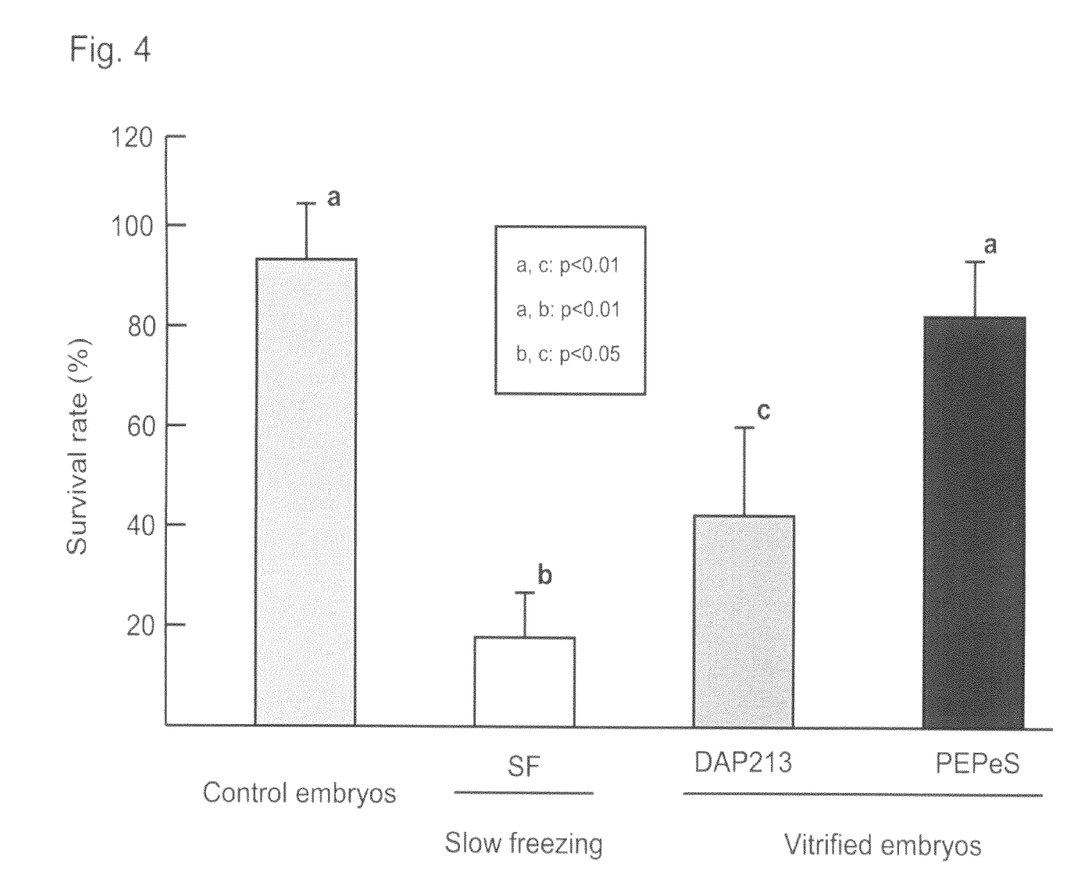
FIG. 4 shows the survival rates of ES cells after thaw that had been preserved via various techniques.

No difference was observed between the control embryos and the embryos preserved in PEPeS (FIG. 4). In contrast, survival rates of the embryos preserved in SF and of the embryos preserved in DAP213 were significantly low. The embryos preserved in PEPeS exhibited a significantly higher survival rate compared with the embryos preserved in DAP213. Even though these techniques involve preservation by vitrification, accordingly, the method of the present invention was found to be more suitable for preserving marmoset ES cells.

Comparison Among a Plurality of Cell Lines

With the use of cell lines No. 40 and No. 20, whether or not the method of the present invention was effective for other cell lines was examined. This examination was carried out by preserving the cells, heating the preserved cells, initiating culture, and observing the cells under an inverted microscope 4 days thereafter to inspect the number of surviving cell clumps.

Figure 5:
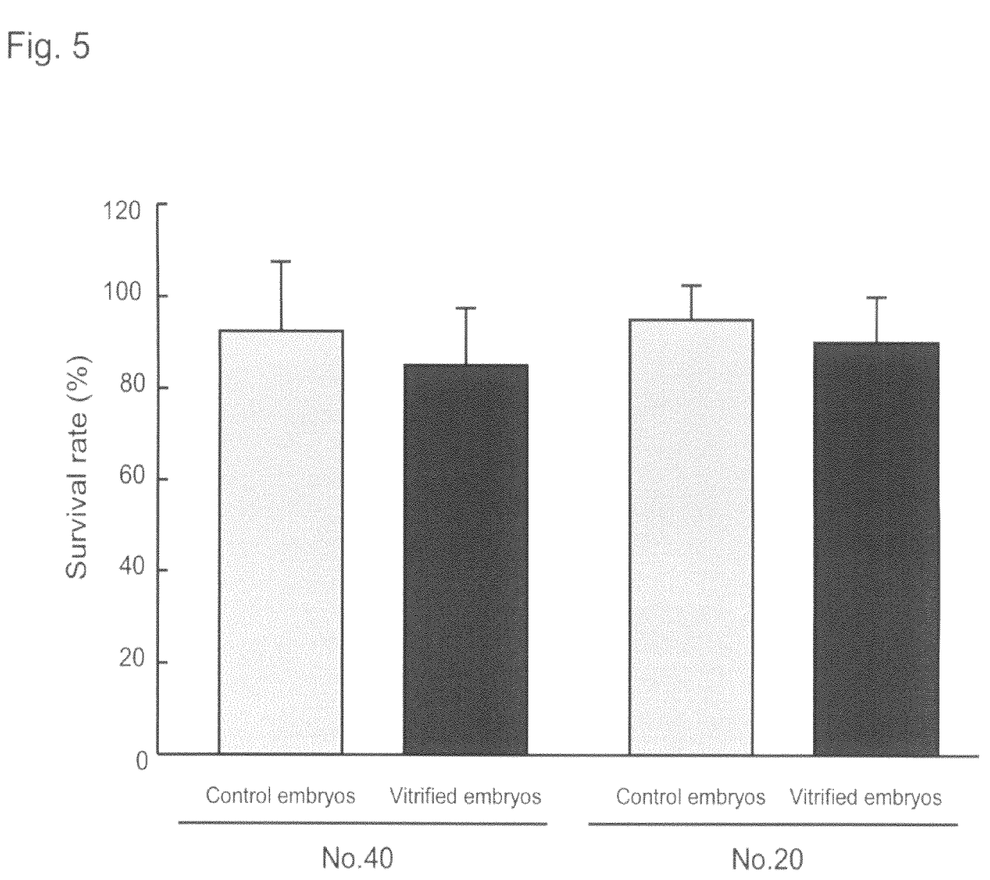
FIG. 5 shows the results of preserving a plurality of ES cell lines by the method of the present invention.

With the use of cell lines No. 40 and No. 20, no significant difference was observed between the control embryos and the embryos preserved by vitrification (FIG. 5).

Maintenance of ES Cell Undifferentiated State after Preservation

With the use of cell lines No. 40 and No. 20, whether or not the ES cells maintained the undifferentiated state after preservation by vitrification and heating was examined. The preserved cell clumps were heated, cultured for a given period of time, and then examined. SSEA-1, SSEA-3, SSEA-4, TRA-1-60, TRA-1-81, and alkaline phosphatase were used as ES cell markers in immunostaining. The thawed cell clumps were transplanted hypodermically to immunodeficient mice (NOD/Scid/γ$^c$null), sampling was carried out 3 months later, and teratoma development by the transplanted cell clumps was observed.

Figure 6:
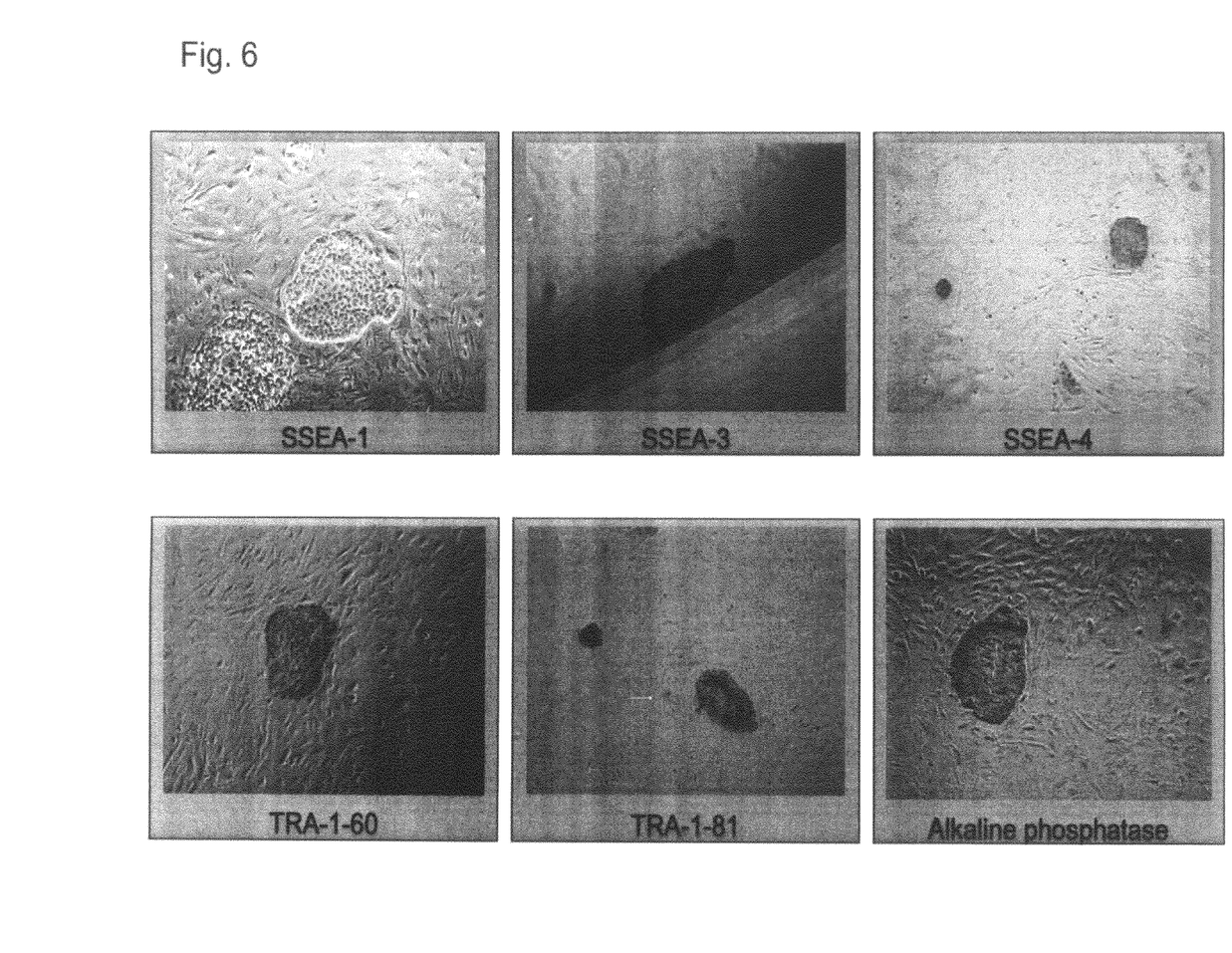
FIG. 6 shows the results of staining the marmoset ES cells preserved by vitrification.
Figure 7:
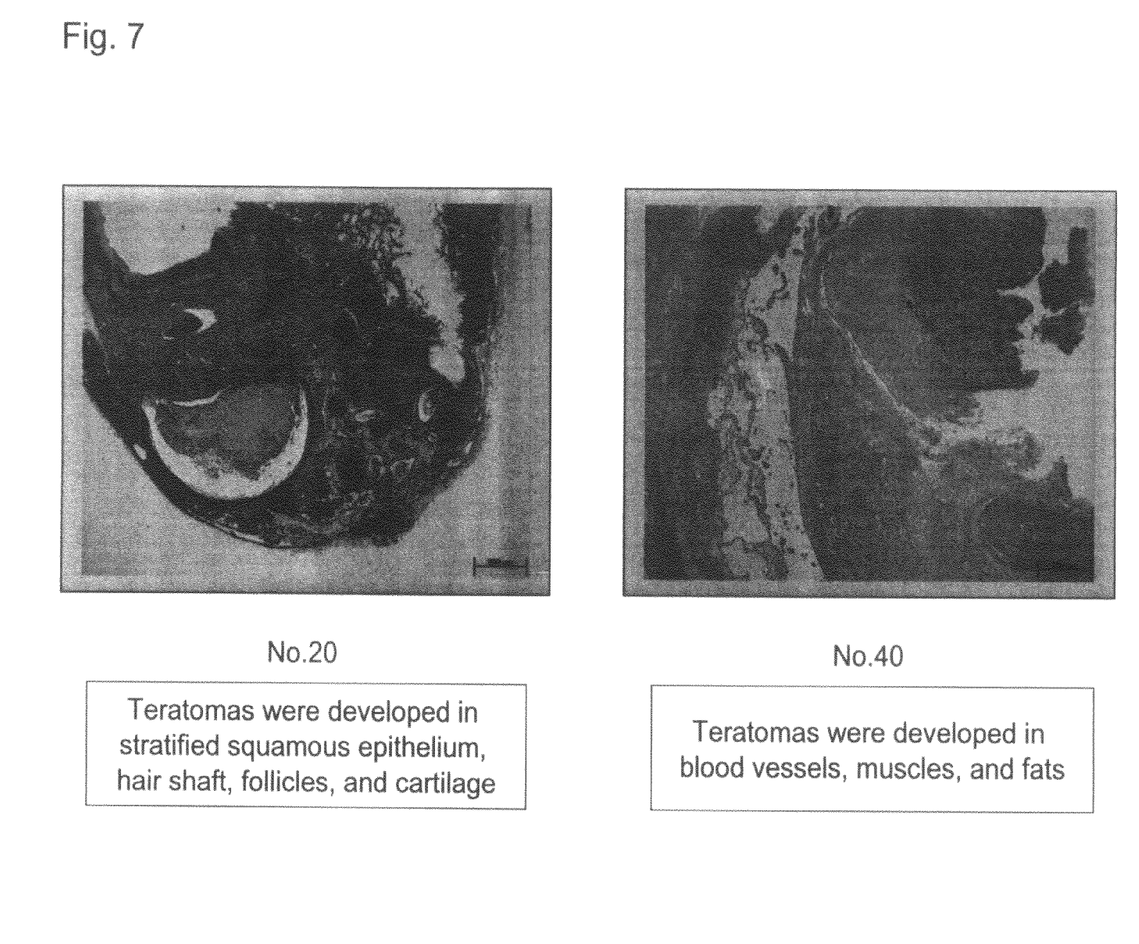
FIG. 7 shows the results of testing teratoma development with the use of the marmoset ES cells preserved by vitrification.

All the staining experiments produced results in accord with those of the report concerning the unpreserved ES cells (Sasaki E. et al., 2005, Establishment of Novel Embryonic Stem Cell Lines Derived from the Common Marmoset (*Callithrix jacchus*), Stem Cells (in press)) (FIG. 6). Via the experiment of teratoma development (FIG. 7), teratoma development was observed in blood vessels, muscles, and fats with the use of the cell line No. 40 and in hair, follicles, cartilage, and squamous epithelium with the use of the cell line No. 20. This was also in accordance with the report concerning the unpreserved cells (Sasaki E. et al., 2005, Establishment of Novel Embryonic Stem Cell Lines Derived from the Common Marmoset (*Callithrix jacchus*), Stem Cells (in press)).

As is apparent from the foregoing description, the method of preservation by vitrification according to the present invention is effective for preserving primate ES cells.

What is claimed is:

1. A method of preserving mammalian early embryos or embryonic stem cells by vitrification, comprising:

pretreating mammalian early embryos or embryonic stem cells in a pretreatment solution comprising a first phosphate buffer comprising a polyhydric alcohol constituent wherein said polyhydric alcohol constituent of the first phosphate buffer consists of 10% to 15% (v/v) propylene glycol;

adding a solution for preservation by vitrification, said solution comprising a second phosphate buffer comprising polyhydric alcohol constituents, wherein said polyhydric alcohol constituents of said second phosphate buffer consist of (1) 10% to 15% (v/v) propylene glycol and (2) 25% to 35% (v/v) ethylene glycol, and wherein said second phosphate buffer further comprises 15% to 25% (v/v) Percoll® and 0.2 M to 0.5 M sucrose, to the mammalian early embryos or embryonic stem cells in the pretreatment solution to obtain a mixture wherein the volume ratio of the pretreatment solution to the solution for preservation by vitrification is 1:99 to 20:80; and cryopreserving the mammalian early embryos or embryonic stem cells in the mixture of the pretreatment solution and the solution for preservation by vitrification.

2. The method of preserving mammalian early embryos or embryonic stem cells by vitrification according to claim 1, wherein the step of pretreating the mammalian early embryos or the embryonic stem cells comprises (1) immersing the mammalian early embryos or embryonic stem cells in the pretreatment solution at room temperature for 5 to 10 minutes; (2) lowering the temperature to 0° to 5° C.; and (3) allowing the pretreatment solution to stand at 0° C. to 5° C. for 30 seconds to 2 minutes; and wherein the volume ratio of the pretreatment solution to the solution for preservation by vitrification in the mixture is 40:60.

3. The method of preserving mammalian early embryos or embryonic stem cells by vitrification according to claim 1, wherein the mammalian early embryos are mammalian 2 cell-stage embryos.

4. The method of preserving mammalian early embryos or embryonic stem cells by vitrification according to claim 3, wherein the mammalian 2-cell-stage embryos are rat 2cell-stage embryos and the mammalian ES cells are primate ES cells.

5. The method of claim 1 for preserving mammalian early embryos or embryonic stem cells by vitrification, wherein the pretreatment solution comprises 700 to 900 mg/100 ml NaCl, 15 to 25 mg/100 ml KCl, 8 to 15 mg/100 ml $CaCl_2$, 15 to 25 mg/100 ml $KH_2PO_4$, 7.5 to 12.5 mg/100 ml $MgCl_2.6H_2O$, 100 to 130 mg/100 ml $Na_2HPO_4$, 3 to 4 mg/100 ml Na pyruvate, 75 to 125 mg/100 ml glucose, 5 to 10 mg/100 ml antibiotics, 250 to 350 mg/100 ml BSA, and 10% to 15% (v/v) propylene glycol.

6. The method of claim 1 for preserving mammalian early embryos or embryonic stem cells by vitrification, wherein the solution for preservation by vitrification comprises 700 to 900 mg/100 ml NaCl, 15 to 25 mg/100 ml KCl, 8 to 15 mg 100 ml $CaCl_2$, 15 to 25 mg/100 ml $KH^2 PO_4$, 7.5 to 12.5 mg/100 ml $MgCl_2.6H_2O$, 100 to 130 mg/100 ml $Na_2HPO_4$, 3 to 4 mg/100 ml Na pyruvate, 75 to 125 mg/100 ml glucose, 5 to 10 mg/100 ml antibiotics, 250 to 350 mg/100 ml BSA, 10% to 15% (v/v) propylene glycol, 25% to 35% (v/v) ethylene glycol, 15% to 25% (v/v) Percoll®, and 0.2 M to 0.5 M sucrose.

7. The method of claim 1 for preserving mammalian early embryos or embryonic stem cells by vitrification, wherein the pretreatment solution is a solution consisting of 700 to 900 mg/100 ml NaCl, 15 to 25 mg/100 ml KCl, 8 to 15 mg/100 ml $CaCl_2$, 15 to 25 mg/100 ml $KH_2PO_4$, 7.5 to 12.5 mg/100 ml $MgCl_2.6H_2O$, 100 to 130 mg/100 ml $Na_2HPO_4$, 3 to 4 mg/100 ml Na pyruvate, 75 to 125 mg/100 ml glucose, 59 to 10 mg/100 ml antibiotics, and 250 to 350 mg/100 ml BSA ;and the solution for preservation by vitrification is a solution consisting of 700 to 900 mg/100 ml NaCl, 15 to 25 mg/100 ml KCl, 8 to 15 mg/100 ml $CaCl_2$, 15 to 25 mg/100 ml $KH_2PO_4$, 7.5 to 12.5 mg/100 ml $MgCl_2.6H_2O$, 100 to 130 mg/100 ml $Na_2HPO_4$, 3 to 4 mg/100 ml Na pyruvate, 75 to 125 mg/100 ml glucose, 5 to 10 mg/100 ml antibiotics, 250 to 350 mg/100 ml BSA, 10% to 15% (v/v) propylene glycol, 25% to 35% (v/v) ethylene glycol, 15% to 25% (v/v) Percoll®, and 0.2 M to 0.5 M sucrose.

8. The method of claim 1 for preserving mammalian early embryos or embryonic stem cells by vitrification, wherein the method is for preserving embryonic stem cells.

* * * * *